(12) United States Patent
Wiley et al.

(10) Patent No.: US 8,035,000 B2
(45) Date of Patent: Oct. 11, 2011

(54) SOYBEAN 75155

(75) Inventors: Hunt B. Wiley, Lafayette, IN (US);
Ronald E. Secrist, Ames, IA (US);
William M. Campbell, Beloit, WI (US);
Robert E. Moore, Gibson City, IL (US);
John Diehl, Dansville, MI (US)

(73) Assignee: Dairyland Seed Co., Inc., West Bend, WI (US)

( * ) Notice: Subject to any disclaimer, the term of this patent is extended or adjusted under 35 U.S.C. 154(b) by 196 days.

(21) Appl. No.: 12/324,198

(22) Filed: Nov. 26, 2008

(65) Prior Publication Data
US 2010/0132061 A1    May 27, 2010

(51) Int. Cl.
*A01H 1/00*    (2006.01)
*A01H 4/00*    (2006.01)
*A01H 5/00*    (2006.01)
*A01H 5/10*    (2006.01)
*C12N 15/82*   (2006.01)

(52) U.S. Cl. ........ 800/312; 800/260; 800/278; 800/279; 800/281; 800/284; 800/298; 800/300; 800/301; 800/302; 800/303; 435/415; 435/426

(58) Field of Classification Search .................. None
See application file for complete search history.

(56) References Cited

U.S. PATENT DOCUMENTS
6,143,954 A    11/2000   Hicks, Jr.

OTHER PUBLICATIONS

Schmitt, D.P. et al., "Differentiating soybean responses to *Heterodera glycines* races," Crop. Sci. (1992) 32:275-277.
Listing of Experimental Use and Sales of 75155 (May 2007-Nov. 2008) 1 page.

*Primary Examiner* — Russell Kallis
(74) *Attorney, Agent, or Firm* — Michael Best & Friedrich LLP

(57) ABSTRACT

Disclosed is the seed of a novel soybean cultivar, designated 75155, a sample of which is deposited under ATCC Accession No. PTA-11596. Also disclosed are plants, or parts thereof, grown from the seed of the cultivar, plants having the morphological and physiological characteristics of the 75155 cultivar, and methods of using the plant or parts thereof in a soybean breeding program.

19 Claims, No Drawings

SOYBEAN 75155

STATEMENT REGARDING FEDERALLY SPONSORED RESEARCH OR DEVELOPMENT

Not applicable.

BACKGROUND OF THE INVENTION

Soybeans are a major grain crop valued for the high levels of oil and protein found in soybean seed. Soybean breeding has resulted in significant improvements in yield potential, stability of yield, adaptation of the species to mechanical harvest, and yield protection through improved disease resistance.

Due to the nature of plant science agriculture, broadly defined as a manipulation of available plant resources to meet the needs of the growing human population, the environment in which plants are grown for agricultural production continuously offers new obstacles to agricultural production. Each new cultivar or variety released to agricultural production is selected for the purpose of increasing yield resulting from increased disease resistance to prevalent diseases, or from direct or indirect improvement in yield potential or efficiency of production. Development of stable, high yielding cultivars with superior characteristics is an ongoing goal of soybean breeders.

There is a need in the art for a novel, superior soybean cultivar and soybean seed.

SUMMARY OF THE INVENTION

In one aspect, the present invention provides a soybean seed designated 75155, wherein a sample of said seed has been deposited under the terms of the Budapest Treaty and in accordance with 37 C.F.R. §§1.801-1.809 on Jan. 20, 2011 with the American Type Culture Collection (ATCC), Manassas, Va., under ATCC Accession No. PTA-11596.

In another aspect, the present invention provides a soybean plant, or a part thereof, produced by growing seed designated 75155, or a soybean plant having the characteristics of a plant produced by growing seed designated 75155, or pollen or an ovule of a soybean plant according to the present invention.

The present invention provides a tissue culture of regenerable cells from a plant, or parts thereof, produced by growing seed designated 75155, and a soybean plant regenerated from the tissue culture.

The present invention also provides a method for developing a soybean plant in a soybean breeding program using plant breeding techniques, comprising using a soybean plant, or part thereof, produced by growing seed designated 75155 as a source of breeding material.

DEFINITIONS

In the claims, descriptions and tables that follow, numerous terms are used and are defined as follows:

Flower color: Modern soybeans are characterized by two major flower colors, purple or white. Some cultivars are heterogeneous for flower color whereby some plants have purple flowers and some have white.

Leaflet shape: The leaflet may be broad or narrow and may be ovate or oval in shape.

Plant habit refers to stem termination in soybeans and the resultant differences in flower production. Indeterminate varieties continue to grow during the reproductive phase, producing new branches and nodes after flowering is well underway. Determinate varieties tend to delay the onset of flowering somewhat, and limit new node and branch development after flowering has been initiated.

Pubescence relates to the plant trichomes or hairs found on the stems, leaves and pods of soybeans.

Pubescence color in modern soybeans may be tawny, gray or light tawny.

Pod color refers to the color of the mature pod wall, as distinct from the color of the pubescence, and in modern soybeans, may be brown or tan.

Hilum refers to the point of attachment of soybean seed to maternal tissue.

Hilum color in modern soybeans may be black, brown, yellow, gray, buff, or imperfect black.

Soybean emergence scores rate the ability of the seedlings to emerge from the soil. A visual score of 1 to 5, taken 10-15 days after planting, is used whereby a score of 1 indicates an excellent emergence vigor and early growth, an intermediate score of 2.5 indicates average ratings, and a 5 score indicates a very poor emergence vigor and early growth.

Plant height is measured from the top of soil to top node of the plant in any convenient unit of length (i.e., inches, centimeters). For the data presented herein, plant height was measured just prior to harvest and is expressed in inches.

Lodging resistance relates to the stature of the plant relative to the ground. Lodging resistance is rated on a scale of 1 to 5. A score of 1 is given to an erect plant. A score of 2.5 is given to a plant that is leaning at a 45-degree angle relative to the ground. A score of 5 indicates a plant lying on the ground.

Maturity date is the date when 95% of pods have turned color from green color to their mature brown or tan color. The maturity date is counted in days and is calculated from January 1.

Maturity group refers to an industry division of groups of varieties based on the zones in which the varieties are adapted. Soybeans mature differentially in response to day-length and thus to latitude where grown. In the soybean production areas of the United States, for example, the northern-most production region of northern Minnesota is planted to soybeans that mature under very long day-lengths during early summer. In the southernmost production regions of the Southeast, soybeans that mature from the influence of short day-length during early summer are grown. Those adapted to northern day-lengths are classified as early-maturing, those adapted to the southern regions are classified as late-maturing. Maturity groups include very long day length varieties (000, 00, 0) and extend to very short day length varieties (VII, VII, IX, X). For example, maturity group I soybean cultivars are typically grown in southern Minnesota, whereas maturity group IV soybean cultivars are typically group in southern Illinois.

Relative maturity: Within maturity groups, a more precise maturity assignment is given that subdivides each maturity group into tenths. For example, a relative maturity of 3.3 is assigned to a late early maturity group III soybean cultivar.

Shattering refers to pod dehiscence prior to harvest resulting in a loss of mechanically harvestable seed. Pod dehiscence involves seeds falling from the pods to the soil. This is visually scored with a 1 to 5 scale comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Yield refers to the yield of seed harvested from a soybean crop. Yield data presented herein is expressed as bushels of seed/acre and is the actual yield of the grain at harvest.

*Phytophthora* tolerance to *Phytophthora* root rot, caused by the fungus, *Phytophthora megasperma* var. *sojae*, is rated on a visual scale of 1 to 5, with a score of 1 being the highest tolerance ranging down to a score of 5 which indicates the plants have no tolerance to *Phytophthora*. The visual score is based on the amount of disease-induced stunting of aboveground growth and is taken during the period 3-5 weeks prior to harvest.

Brown Stem Rot (BSR) resistance is a visually scored from 1 to 5 based on interveinal leaf chlorosis (yellowing) and necrosis due to brown stem rot, which is caused by the fungus, *Phialophora gregata*. A score of 1 indicates no symptoms. Visual scores range to a score of 5 that indicates severe symptoms of interveinal leaf chlorosis and necrosis. Plants receiving scores of 1.0-1.6 are classified as resistant; plants receiving scores of 1.7-2.0 are classified as moderately resistant.

Sclerotinia Stem Rot (SSR) is a soil-borne fungal disease that causes above-ground disease in soybeans. Plants are infected via discharged ascospores that successfully germinate and infect through soybean structures such as flower petals. Colonization of stem tissue ultimately results in loss of yield potential. Cultivars are rated using prevalence and severity scores and converted into an estimated percent yield loss that can be used for comparison to known resistant or susceptible cultivar standards.

Soybean Cyst Nematode (SCN) resistance is based on a comparison of reproduction rates to a known susceptible cultivar as described by Schmitt et al. (Crop Sci. 32:275-277, 1992), which is incorporated by reference herein. A cultivar with a 0-10% percent reproductive rate compared to a known susceptible cultivar is classified as resistant (R); a cultivar with an 11-30% reproductive rate compared to a known susceptible cultivar is classified as moderately resistant (MR); a cultivar with an 31-59% reproductive rate compared to a known susceptible cultivar is classified as moderately susceptible (MS).

Iron-Deficiency Chlorosis (IDC) results when soybeans lack adequate iron. A visual score taken 25-30 days after planting is used to rate iron-deficiency chlorosis. A score of 1 indicates no stunting of the plants or chlorosis of the leaves, and a score of 5 indicates the plants are dead or dying as a result of iron-deficiency chlorosis. A score of 2.5 means plants have intermediate health with some leaf chlorosis.

Seed Size is measured by seed number per pound of seed. Seed size is a heritable trait but is influenced by environment, and as such, is often presented as a comparison to another variety.

DETAILED DESCRIPTION OF THE INVENTION

Soybean cultivar 75155 has superior characteristics and was developed from crossing two elite soybean varieties. Criteria used to select in various generations included seed yield, lodging resistance, emergence, disease resistance and tolerance, maturity, late season plant intactness, plant height, shattering resistance, and seed astringency. "Astringency," as used herein with reference to soybean seed, refers to a taste sensation perceived as a puckering, rough, bitter, and/or drying mouth-feel. Astringency can be perceived as a negative attribute of soybean seed food products, including for example soymilk. As such, reduced astringency of soybean seed can be a desirable trait. Astringency can be measured by sensory evaluation using any of a variety of methodologies generally known in the art.

$F_1$ and $F_2$ plants were advanced by a modified single seed descent selection. In the winter, $F_2$-derived $F_3$ plants were grown into F3 progeny rows for single plant selection. $F_4$ plant rows from F3 single plant selections were grown in the US for evaluation and seed bulking. F4 row 5R2537-46 was identified as superior. Seed from 5R2537-46 was harvested and bulked. The line, now known as 75155, was tested at 18 Midwest locations for yield and agronomic evaluation and at ten Midwest locations for disease reactions. Extensive testing of 75155 for agronomic and disease evaluations were performed at many locations over two years.

Soybean cultivar 75155 is a mid-maturity group II variety, with a relative maturity of 2.4. The cultivar has very high yield potential, relative to lines of similar maturity, and excellent agronomic characteristics, including lodging resistance. Soybean cultivar 75155 is a conventional soybean cultivar and is not resistant to the Roundup™ herbicides. Soybean cultivar 75155 is well-adapted to early maturity group II to early maturity group III growing areas of Michigan, Ohio, Indiana, Iowa, Illinois, Minnesota, South Dakota, Nebraska and Wisconsin.

Soybean cultivar 75155 has uniformity and stability of its morphological and other characteristics. The variety description information (Table I) provides a summary of characteristics of soybean cultivar 75155 plant characteristics. As used herein, "a soybean plant having the physiological and morphological characteristics of soybean cultivar 75155" is a plant having the characteristics set forth in Table 1.

TABLE 1

VARIETY DESCRIPTION INFORMATION

| | |
|---|---|
| Seed coat color: | Yellow |
| Hilum color: | Yellow |
| Leaflet size: | Medium |
| Leaflet color: | Medium-green |
| Leaflet shape: | Ovate |
| Flower Color: | Purple |
| Plant habit: | Indeterminate |
| Pubescence color: | Gray |
| Pod color: | Brown |
| Maturity group: | II |
| Relative maturity: | 2.4 |
| *Phytophthora* Root Rot resistance: | none |
| Brown Stem Rot (*Phialophora gregata*): | Resistant |
| Soybean Cyst Nematode Disease: | Susceptible |
| Iron Deficiency Chlorosis Tolerance: | 2.9 |

In addition to the individual plant characteristics set forth above in Table 1, agronomic properties of cultivar 75155 were evaluated. The cultivar has adequate ratings for the following characteristics: emergence (1.1), *Phytophthora* Root Rot tolerance (1.9), and Sclerotinia Stem Rot resistance (1.2). Table 2 compares agronomic properties of soybean cultivar 75155 for 2006-2007 to those of several competing varieties of commercial soybeans of similar maturity. The agronomic properties compared include lodging (Lod), *Phytophthora* Root Rot Tolerance (PRR Tol), percent yield reduction due to Sclerotina stem rot disease (SSR-%), iron deficiency chlorosis (IDC) rating, and average plant height, in inches. Table 3 compares the yield and maturity date of various cultivars.

TABLE 2

Summary of agronomic properties of soybean cultivar 75155, compared to several competing varieties of commercial soybeans of similar maturity.

| Years | Cultivar | Lod | PRR Tol | SSR-% | IDC | HT |
|---|---|---|---|---|---|---|
| 1 | 75155RR | 1.6 | | | 2.8 | 34 |
| | VINTON 81 | 3.0 | | | 2.8 | 41 |
| 1 | 75155RR | 2.0 | 2.0 | | | 36 |
| | S18-N5 | 1.2 | 2.0 | | | 32 |

TABLE 2-continued

Summary of agronomic properties of soybean cultivar 75155, compared to several competing varieties of commercial soybeans of similar maturity.

| Years | Cultivar | Lod | PRR Tol | SSR-% | IDC | HT |
|---|---|---|---|---|---|---|
| 2 | 75155RR | 1.6 | 3.5 | 6.4 | 3.1 | 35 |
|   | S20-F8   | 1.4 | 2.5 | 4.4 | 2.8 | 36 |
| 1 | 75155RR | 1.6 | 3.5 | 6.4 | 3.5 | 35 |
|   | S25-J5   | 1.2 | 2.5 | 6.3 | 3.7 | 34 |
| 1 | 75155RR | 1.4 | 2.0 |     |     | 35 |
|   | A2442    | 1.2 | 2.5 |     |     | 39 |
| 2 | 75155RR | 1.6 | 3.5 | 6.4 | 3.1 | 35 |
|   | A2553    | 1.3 | 2.5 | 10.1| 3.2 | 32 |
| 2 | 75155RR | 1.6 |     |     | 2.8 | 34 |
|   | A3244    | 1.5 |     |     | 2.9 | 39 |

TABLE 3

Summary of yield and maturity data of soybean cultivar 75155 and other varieties of commercial soybeans.

| Years | Cultivar | Reps | Yield | Mat Days |
|---|---|---|---|---|
| 1 | 75155RR  | 13 | 55.4 | 268 |
|   | VINTON 81|    | 41.8 | 267 |
| 1 | 75155RR  | 6  | 41.2 | 267 |
|   | S18-N5   |    | 41.1 | 262 |
| 2 | 75155RR  | 25 | 53.3 | 264 |
|   | S20-F8   |    | 47.0 | 259 |
| 1 | 75155RR  | 16 | 49.5 | 257 |
|   | S25-J5   |    | 51.1 | 253 |
| 1 | 75155RR  | 12 | 44.4 | 265 |
|   | A2442    |    | 45.4 | 264 |
| 2 | 75155RR  | 25 | 53.3 | 264 |
|   | A2553    |    | 44.0 | 264 |
| 2 | 75155RR  | 17 | 53.0 | 266 |
|   | A3244    |    | 53.5 | 274 |

The present invention contemplates using the 75155 soybean plant, or part thereof, or a soybean plant having the physiological and morphological characteristics of the soybean plant, as a source of breeding material for developing a soybean plant in a soybean breeding program using plant breeding techniques. Plant breeding techniques useful in the developing soybean plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature. For example, see U.S. Pat. No. 6,143,954, which, along with the references cited therein, is incorporated by reference herein.

As used herein, the term "plant" includes plant cells, plant protoplasts, plant cell tissue cultures from which soybean plants can be regenerated, plant calli, plant clumps, and plant cells that are intact in plants or parts thereof. "Plant part" includes, but is not limited to, embryos, pollen, ovules, seeds, flowers, pods, leaves, roots, root tips, anthers, and the like.

One may obtain soybean plants according to the present invention by directly by growing the seed of 75155 or by any other means. A soybean plant having all of the physiological and morphological characteristics of 75155 can be obtained by any suitable means, including, but not limited to, regenerating plants or plant parts from tissue culture or cuttings. The scope of the present invention is not limited by the method by which the plant is obtained.

Deposit Information

Seed from soybean cultivar 75155, disclosed above and recited in the appended claims, was deposited with the American Type Culture Collection (ATCC), 10801 University Boulevard, Manassas, Va. 20110 on Jan. 20, 2011 as PTA-11596. The seeds deposited were taken from seeds maintained by Dairyland Seed Co., Inc., West Bend, Wis. 53095 since prior to the filing date of this application. Access to the ATCC deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. Applicant has or will have satisfied all of the requirements of 37 C.F.R. §§1.801-1.809.

The present invention is not limited to the exemplified embodiments, but is intended to encompass all such modifications and variations as come within the scope of the following claims.

We claim:

1. A soybean seed designated 75155, wherein a sample of said seed has been deposited under ATCC Accession No. PTA-11596.

2. A plant, or a part thereof, produced by growing the seed of claim 1.

3. Pollen of the plant of claim 2.

4. An ovule of the plant of claim 2.

5. A soybean plant, or a part thereof, having all the physiological and morphological characteristics of the soybean plant of claim 2.

6. A tissue culture of regenerable cells from the plant, or part thereof, of claim 2.

7. The tissue culture of regenerable cells of claim 6 selected from the group consisting of protoplasts and calli, wherein the regenerable cells are derived from leaf, pollen, ovule, cotyledon, hypocotyl, embryo, root, pod, flower, shoot and stalk.

8. A soybean plant regenerated from the tissue culture of claim 6, wherein the plant has all of the physiological and morphological characteristics of a plant produced by growing seed designated 75155 and deposited under ATCC Accession No. PTA-11596.

9. A tissue culture of regenerable cells from the plant, or part thereof, of claim 5.

10. The tissue culture of claim 9, wherein the regenerable cells selected from the group consisting of protoplasts and calli and wherein the regenerable cells are derived from a plant part selected from the group consisting of leaf, pollen, ovule, cotyledon, hypocotyl, embryo, root, pod, flower, shoot and stalk.

11. A soybean plant regenerated from the tissue culture of claim 9, wherein the plant has all of the physiological and morphological characteristics of a plant produced by growing seed designated 75155 and deposited under ATCC Accession No. PTA-11596.

12. A method for developing a soybean plant in a soybean breeding program using plant breeding techniques, comprising using the soybean plant, or part thereof, of claim 2 as a source of breeding material.

13. The method of claim 12 wherein said plant breeding techniques are selected from the group consisting of single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation.

14. A method for developing a soybean plant in a soybean breeding program using plant breeding techniques, comprising using the soybean plant, or part thereof, of claim 5 as a source of breeding material.

15. The method of claim 14 wherein said plant breeding techniques are selected from the group consisting of single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation.

16. A method for producing a soybean cultivar 75155-derived soybean plant, comprising:
(a) crossing the plant of claim 2 which is produced by growing a soybean seed deposited as ATCC Accession No. PTA-11596 with a second soybean plant to yield progeny soybean seed; and
(b) growing said progeny seed to yield a soybean cultivar 75155-derived soybean plant.

17. A soybean cultivar 75155-derived soybean plant, or parts thereof, produced by the method of claim 16.

18. The method of claim 16, further comprising
(c) crossing the soybean cultivar 75155-derived soybean plant of (b) with itself or another soybean plant to yield an additional soybean cultivar 75155-derived soybean progeny seed; and
(d) growing the progeny soybean seed of (c) to yield additional soybean cultivar 75155-derived soybean plants.

19. The method of claim 18, wherein (c) and (d) are repeated at least one time to generate additional soybean cultivar 75155-derived soybean plants.

* * * * *